United States Patent
Manfred

(10) Patent No.: US 8,045,144 B2
(45) Date of Patent: Oct. 25, 2011

(54) APPARATUS AND METHOD FOR THE INSPECTION OF THE SURFACE OF A COMPONENT

(75) Inventor: Baumgartner Manfred, Berlin (DE)

(73) Assignee: Rolls-Royce Deutschland Ltd & Co KG (DE)

( * ) Notice: Subject to any disclaimer, the term of this patent is extended or adjusted under 35 U.S.C. 154(b) by 324 days.

(21) Appl. No.: 12/320,076

(22) Filed: Jan. 16, 2009

(65) Prior Publication Data
US 2009/0185177 A1 Jul. 23, 2009

(30) Foreign Application Priority Data
Jan. 22, 2008 (DE) .......... 10 2008 005 554

(51) Int. Cl.
*G01N 21/00* (2006.01)
(52) U.S. Cl. ............................. 356/237.1; 356/237.2
(58) Field of Classification Search ..... 356/237.2–237.6
See application file for complete search history.

(56) References Cited

U.S. PATENT DOCUMENTS

| | | |
|---|---|---|
| 7,146,291 B2 | 12/2006 | Hough |
| 2002/0080344 A1* | 6/2002 | Tomita et al. ............ 356/237.1 |
| 2002/0089298 A1 | 7/2002 | Hatley et al. |
| 2004/0021856 A1* | 2/2004 | Nishiyama et al. ....... 356/237.2 |
| 2006/0236769 A1 | 10/2006 | Tenley et al. |
| 2007/0089545 A1 | 4/2007 | Roney et al. |

OTHER PUBLICATIONS

European Search Report dated Dec. 30, 2010 from the counterpart European application.

* cited by examiner

*Primary Examiner* — Tri T Ton
(74) *Attorney, Agent, or Firm* — Timothy J. Kilma; Shuttleworth & Ingersoll, PLC

(57) ABSTRACT

An apparatus for inspection of a surface of a component includes a probing device (21) which is coupled to a traversing device (50) and has at least one probe carrier (22, 23), to which at least one inspection mechanism is fitted. In order to enable surface defects in a component (11) to be shown directly and without conversion, the inspection mechanism is an image pick-up unit (26, 27).

19 Claims, 2 Drawing Sheets

APPARATUS AND METHOD FOR THE INSPECTION OF THE SURFACE OF A COMPONENT

Figure 1:
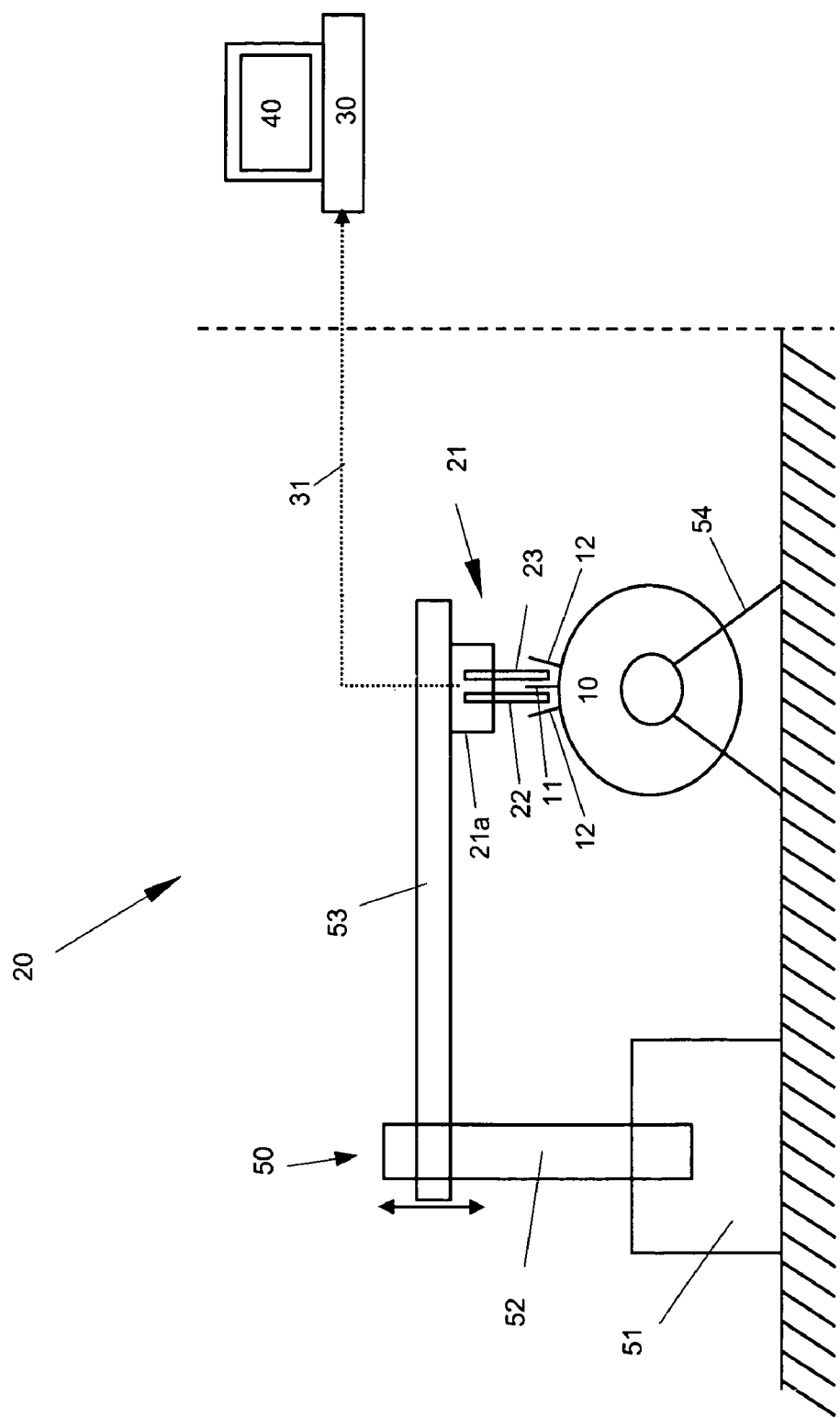

This application claims priority to German Patent Application DE102008005554.9 filed Jan. 22, 2008, the entirety of which is incorporated by reference herein.

The present invention relates to an apparatus for the inspection of the surface of a component. Furthermore the invention relates to the use of the apparatus for inspecting the surface of a component. The invention also applies to a method for the inspection of the surface of a component.

Various options are known for the inspection of the surface of a component. The simplest one is visual inspection for surface defects using a microscope. For this purpose, the use of camera equipment is also known. Furthermore, measuring instruments for determining the dimensions of a component or the peak-to-valley height of the surface are known.

Detection of surface defects is crucial in particular for the blades of a gas turbine. Surface defects can, for example, occur during grinding of blade tips when emitted sparks hit the blade surface (spatter). Also, surface defects can occur in the form of scratches, irregularities or contamination. These surface defects can, in operation, be the origin of cracks which may result in component failure.

In the case of conventional blades, which are individually fitted to a rotor disk, each single blade is completely microscopically inspected at final inspection after production and prior to assembly.

Such inspection is not possible on blades which are integral with a rotor disk in the form of a blisk as they are machined from a solid blank. In this case, the blades are arranged closely to each other and hide each other so that they are only inadequately inspectable by conventional measuring equipment and methods (for example microscopes, cameras). Accordingly, the density of the blades staggered on a blisk makes it impossible that each single blade is completely microscopically inspected for surface defects. Therefore, surface defects are only detectable in the accessible peripheral areas. So far, surface defects in the inaccessible areas between the blades were not inspected, and were almost unassessable, since no suitable inspection method was available. Surface defects in the poorly accessible areas were partly detected only by chance. This constitutes an operational risk and can lead to damage, such as cracks, or to complete failure of a blade.

Specification U.S. Pat. No. 6,907,358 B2 describes a method for the inspection of material defects in components using eddy current. Here, a probe with an electric coil and a component are moved relative to each other by two multi-axial traversing units. An alternating current is generated in the electric coil, which produces eddy current in the component. The probe is moved along the surface of a component and measures the interaction between the electromagnetic field in the coil and the component. At surface defects, the eddy current is disturbed and the excitation current in the coil is changed. Each change allows conclusions to be drawn on the properties of surface defects. However, this method is extremely expensive due to the two multi-axial traversing units. Moreover, the apparatus provides information on the surface defects only indirectly and only upon conversion of the eddy current values.

Specification U.S. Pat. No. 7,146,291 B2 describes a method and an apparatus providing for computerized measurement of the geometry of a blade on a blisk. First, the blisk is fitted to a rotary table. A probe with measuring head is then approached to the blade until the measuring head has contact. A signal is then sent to a computer which determines the co-ordinates of the measuring point. By use of CAD or CAM data, the measuring head is moved along the surface of the component, thus successively determining a required number of measuring points on the blisk surface.

Specification US 2003/0223082 A1 discloses an apparatus and a method for the measurement of a surface contour of a component by an optical system. Here, the component is placed in a container filled with liquid. Then, the component is illuminated and the light reflected from the component surface received by a CCD camera. The light reflected from the component is related to the light reflected from a reference surface. A gray-shade image is obtained which is used to produce a topographic or color-graded view of the surface contour. The result is a complete lateral view of the component.

The state of the art according to the two latter publications does, however, not provide for the detection of surface defects. The apparatuses only provide for dimensional inspection of the component.

A broad aspect of the present invention is to provide an apparatus and a method to enable surface defects in a component to be shown directly and without conversion.

The present invention accordingly provides for an apparatus for inspecting the surface of a component by a probing device which is coupled to a traversing device and has at least one probe carrier to which at least one inspection mechanism is fitted. The inspection mechanism is an image pick-up unit.

The image pick-up unit enables a microscopically exact image of the surface defects of a component to be produced. This enables the surface defects to be reworked accordingly. An increase in operational safety is thus obtained. Moreover, the apparatus enables surface defects, which can occur at any time, i.e. also in operation, to be detected at a maintenance activity. This lowers maintenance costs, as expensive components need not be replaced on spec, and, with regard to all the human and financial consequences incurred by damage, increases operational safety.

In particular, the image pick-up unit can be a digital pick-up unit. The digital pick-up unit enables processing of the image data in electronic form.

Furthermore, the image pick-up unit can be rotatable about at least one axis. This enables both the radii of the roundings, for example at the transition between blade and disk, which are subject to particularly high stresses and the typically curved surfaces of the blades, to be optimally inspected.

Preferably, the probe carrier is smaller than the distance between the component and an adjacent component. This property enables the probe to be introduced, in particular, in spaces to inspect the surfaces thereof.

In an advantageous embodiment of the present invention, the probe carrier is rod-type and the image pick-up unit fitted to the probe carrier at an end of the latter which is facing away from the traversing device. This embodiment provides for ease of manufacture and is well suitable of being introduced into spaces to inspect the surfaces thereof. In particular, one of the image pick-up units can be arranged on the front of the end of the probe, enabling, for example, the bottom of a space to be inspected (for example during servicing).

Alternatively, two probe carriers can be provided in parallel arrangement, with the distance of the probe carriers exceeding the thickness of the component, and each probe carrier being smaller than the distance between the component and an adjacent component. Two parallel probe carriers enable two surfaces within confined spaces on the component to be simultaneously inspected.

In particular, one image pick-up unit each can be arranged on the sides of the probe carrier facing each other. This arrangement allows two opposite surfaces to be simultaneously inspected.

In an embodiment according to the present invention, the probe carriers of the probing device can be rod-type and at least one image pick-up unit can be arranged on at least one probe carrier on at least one end of the latter which is facing away from the traversing device. This embodiment provides for ease of manufacture and is particularly suitable for the inspection of surfaces within spaces.

Preferably, the distance of at least one probe carrier to the component is adjustable. Adjustability enables also those components to be positively inspected whose thickness varies heavily along the travelling path of the probe.

In particular, at least one distance sensor is arranged on the probe carrier. The distance sensor enables the distance between the image pick-up unit and the component to be controlled so that a constant distance to the component can be set and collision avoided.

In a further development of the present invention, the probe carrier is rotatable about at least one axis. Rotatability enables even complexly shaped surfaces to be positively inspected.

Furthermore, lines can be accommodated in the probe carrier which connect the image pick-up unit with a recorder connected to an image analyzing unit. Accommodation of the lines in the probe prevents the lines from being damaged. Recorder and image analyzing unit are used for processing the image data received by the image pick-up unit.

Alternatively, the probe carrier can be provided with at least one data transmitter. Wireless transmission of data via the data transmitter is a space-saving option which, in particular, avoids the design problem of the probe carrier rotating about its own axis and the data line being externally fixed. For this, a miniature data transmitter which radios the data to the recorder is connected downstream of the image pick-up unit.

Preferably, at least one illuminant is arranged on the probe carrier. The illuminant enables surface sections to be lighted which would be shadowed with external illumination.

The apparatus is especially suitable for inspecting the surface of a component with restricted accessibility.

The component can, for example, be a blade of a turbomachine.

In particular, the component can be a blade arranged on a blisk of a gas turbine.

Furthermore, solution is provided by a method for inspecting the surface of a component by use of the apparatus. The image pick-up unit receives image data from the surface of the component and transmits them to a recorder which stores the image data and forwards them to an image analyzing unit. This enables the image data to be stored, processed and analyzed.

In particular, the data transmitter provides for wireless transmission of the image data from the image pick-up unit to the recorder. With wireless transmission of data, data lines can be dispensed with and the design problem of the probe carrier rotating about its own axis and the data line being externally fixed is avoided.

Preferably, the image analyzing unit will automatically detect surface defects of the component. This enables the surface of the component to be rapidly inspected.

Furthermore, the image analyzing unit can store and/or display the position of surface defects in the form of three-dimensional coordinates. Definition of coordinates is advantageous for subsequent rework of areas with surface defects.

The image data are preferably received continuously, i.e. the surface of the component is scanned.

The present invention is more fully described in light of the accompanying drawings showing a preferred embodiment. In the drawings, FIG. 1 is a schematic representation of the apparatus, and FIG. 2 is a schematic representation of the probing device.

FIG. 1 shows the apparatus 20 including a traversing device 50, a probing device 21, a retaining fixture 54, a recorder 30 and an image analyzing unit 40. FIG. 1 further shows a blisk 10 with a blade 11 to be inspected and two adjacent blades 12.

The traversing device 50 is program-controlled and includes a traversing drive 51, a vertical beam 52 and a horizontal beam 53. The horizontal beam 53 is arranged moveably along the vertical beam 52. Arranged at the end of the horizontal beam 53 is the probing device 21.

Figure 2:
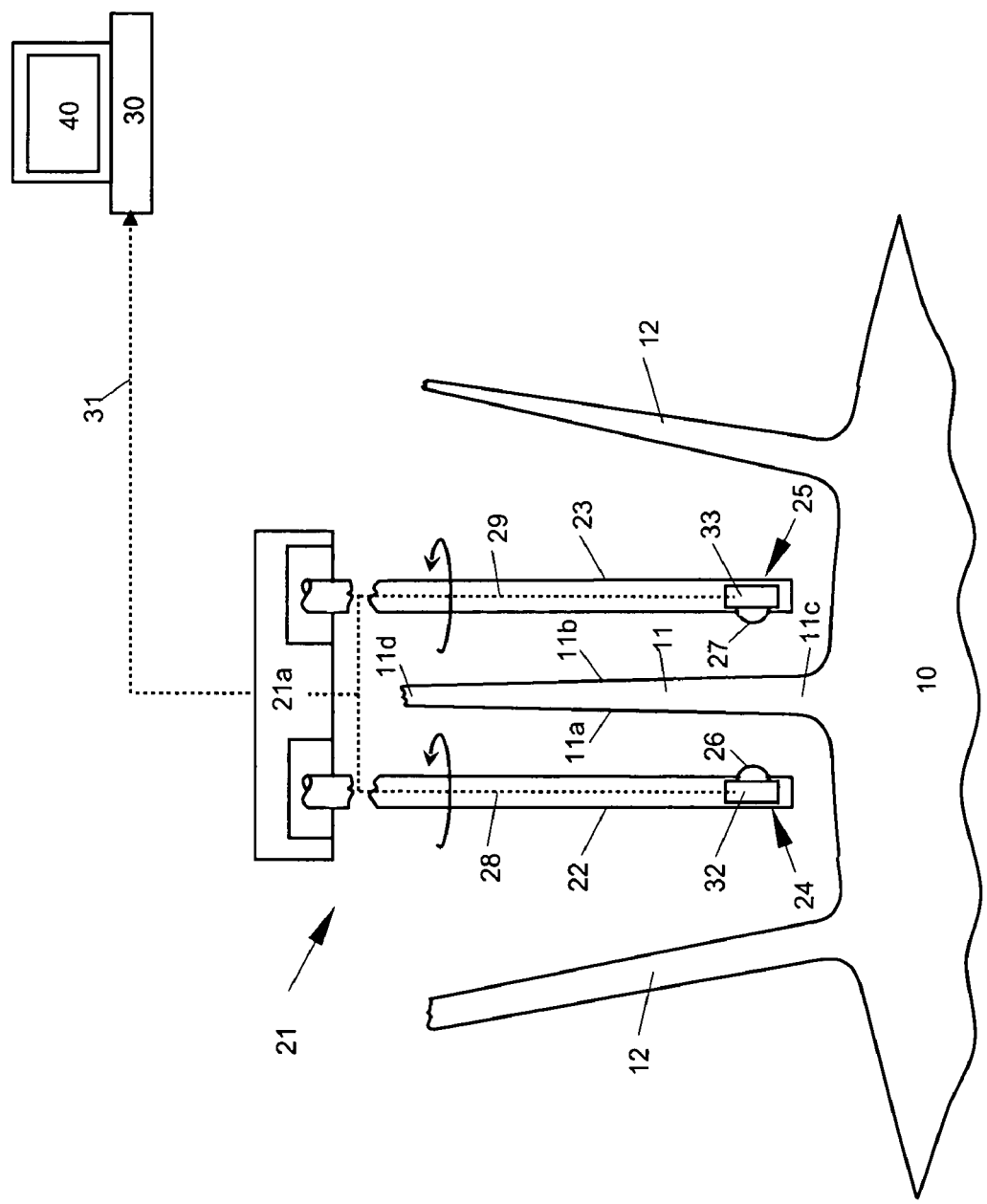

The probing device 21 includes a drive unit 21a for a first probe carrier 22 and a second probe carrier 23 and is shown in enlarged representation in FIG. 2. The probe carriers include image pick-up units 26 and 27 shown in FIG. 2 to which data lines 28 and 29 are connected which are connected to the data line 31. The data line 31 leads to the recorder 30. The recorder 30 is connected to the image analyzing unit 40 via a further data line not shown.

The retaining fixture 54 has the form of a bearing pedestal. The blisk 10 is in the retaining fixture 54, with the blade 11 being in a vertical upward position. FIG. 2 shows a part of the blisk 10. Further shown are the probing device 21, the recorder 30 and the image analyzing unit 40 of the apparatus 20.

The blisk 10 includes integrally formed, radially arranged blades 11 and 12. The blade 11, which is being inspected, has a first surface 11a and a second surface 11b. The first surface 11a and the second surface 11b are opposite to each other and, together, form an aerodynamic profile. Furthermore, the blade 11 has an end 11c which is located radially inwards on the blisk 10 and an end 11d which is oriented radially outwards. The other blades 12 have the same form as the blade 11.

The probing device 21 includes the drive unit 21a, the first probe carrier 22 with the first image pick-up unit 26 (probe) and the first data line 28 as well as the second probe carrier 23 with the second image pick-up unit 27 (probe) and the second data line 29. Alternatively to the two data lines 28 and 29, a first data transmitter 32 can be integrated into the first probe carrier 22 and a second data transmitter 33 into the second probe carrier 23.

The first probe carrier 22 and the second probe carrier 23 of the probing device 21 are rod-type and arranged in parallel to each other. The length of the probe carriers 22, 23 exceeds the length of the blades 11, 12. The image pick-up units 26 and 27 have the form of miniature scanning heads or photocells with high magnification and high resolution for measuring surface defects in the range of 0.01 mm.

The first image pick-up unit 26 is arranged on the first probe carrier 22 on an end 24 of the latter disposed towards the blade end 11c and is directed to the surface 11a of the blade 11. The first image pick-up unit 26 is connected to the first data line 28. Part of the first data line 28 is longitudinally arranged in the interior of the rod-type probe carrier 22. The first data line 28 connects the first image pick-up unit 26 to the data line 31 of the recorder 30. Alternatively to the first data line 28, the first data transmitter 32 can be connected to the first image pick-up unit 26.

The second image pick-up unit 27 is arranged on the second probe carrier 23 on an end 25 of the latter disposed towards the blade end 11c and is directed to the surface 11b of the blade 11. The second image pick-up unit 27 is connected to the second data line 29. Part of the second data line 29 is longitudinally arranged in the interior of the rod-type probe carrier 23. The second data line 29 connects the second image pick-up unit 27 to the recorder 30. Alternatively to the second data line 29, the second data transmitter 33 can be connected to the second image pick-up unit 27.

The data lines 28 and 29 are connected to the recorder 30 via a data line 31. If the data transmitters 32, 33 are used, the data line 31 is dispensable. The image analyzing unit 40 of the apparatus 20 has an image analyzing program and is connected to the recorder 30 via a data line not shown.

Before the blade 11 is inspected for surface defects by the probing device 21, the blisk 10 is placed into the retaining fixture 54 and the blade 11 brought into an upward vertical position (cf. FIG. 1). Then, the traversing drive 51 moves the horizontal beam 53 along the vertical beam 52, thereby moving the probing device 21 with the probe carriers 22 and 23 arranged on the end of the horizontal beam 53 in a program-controlled way into an initial position.

The initial position of the probe carriers 22 and 23 can, for example, be on the blade leading edge at the radially inner end 11c of the blade 11. The probe carriers 22 and 23 of the probing device 21 are here positioned in the areas between the blade 11 and the adjacent blades 12. Accordingly, the two probe carriers 22 and 23 enable the badly accessible surfaces 11a and 11b to be inspected. The drive unit 21a enables the probe carriers 22 and 23 to be rotated about their own axes.

From the initial position, the image pick-up units 26 and 27 in the probe carriers 22 and 23 are first moved transversely from the blade leading edge to the blade trailing edge, i.e. into the image plane or out of the image plane, respectively. In the process, the first image pick-up unit 26 scans a strip of the first surface 11a and the second image pick-up unit 27 scans a strip of the second surface 11b. Upon reaching the blade trailing edge, the probing device 21 is moved radially outwards by the width of the scanned strip and then from the blade trailing edge to the blade leading edge. In the process, one further strip on the surfaces 11a and 11b is scanned by the image pick-up units 26 and 27, respectively. From there, the image pick-up units 26 and 27 will again be moved radially outwards by the width of the scanned strip.

These movements of the image pick-up units 26 and 27 in the probe carriers 22 and 23 are repeated until the image pick-up units 26 and 27 have reached the radially outward end 11d of the blade 11 and the surfaces 11a and 11b have been scanned throughout. The movements of the probe carriers 22 and 23 are each adapted to the actual shape of the surfaces 11a and 11b and can be determined by use of CAD data.

A distance sensor can provide for constant distance of the image pick-up units 26 and 27 to the surfaces 11a and 11b. Also, illuminants can be provided on the probe for good illumination during scanning.

The image data received by the first image pick-up unit 26 are fed to the recorder 30 via the first data line 28 and the data line 31 or by way of wireless transmission (e.g. wireless LAN) using the first data transmitter 32. The image data received by the second image pick-up unit 27 are fed to the recorder 30 via the second data line 29 and the data line 31 or by way of wireless transmission (e.g. wireless LAN) using the second data transmitter 33.

In the recorder 30, the image data is buffered. Upon buffering, the image data is forwarded via the date line not shown to the image analyzing unit 40. Using the image data, the image analyzing program of the image analyzing unit automatically finds defects in the surfaces 11a and 11b. The image data can be provided, for example, with scaling or graduation and display three-dimensional coordinates.

LIST OF REFERENCE NUMERALS

10 Blisk
11 Blade
11a First surface
11b Second surface
11c End
11d End
12 Blade
20 Apparatus
21 Probing device
21a Drive unit
22 First probe carrier
23 Second probe carrier
24 End
25 End
26 First image pick-up unit
27 Second image pick-up unit
28 First data line
29 Second data line
30 Recorder
31 Data line
32 First data transmitter
33 Second data transmitter
40 Image analyzing unit
50 Traversing device
51 Traversing drive
52 Beam
53 Beam
54 Retaining fixture

What is claimed is:

1. An apparatus for inspection of a surface of a component, comprising:
   a traversing device;
   a probing device coupled to the traversing device and including two probe carriers;
   at least one image pick-up unit fitted to the probe carriers;
   the two probe carriers provided in parallel arrangement, with a distance between the probe carriers exceeding a thickness of the component, and each probe carrier being smaller than a distance between the component and an adjacent component.

2. The apparatus of claim 1, comprising one image pick-up unit each arranged on sides of the two probe carriers facing each other.

3. The apparatus of claim 2, wherein the probe carriers are rod-type and that at least one image pick-up unit is fitted to at least one probe carrier at one end thereof facing away from the traversing device.

4. The apparatus of claim 3, wherein a distance of at least one probe carrier to the component is adjustable.

5. The apparatus of claim 4, wherein the image pick-up unit is a digital pick-up unit.

6. The apparatus of claim 5, wherein the image pick-up unit is rotatable about at least one axis.

7. The apparatus of claim 4, comprising at least one distance sensor arranged on the probe carrier.

8. The apparatus of claim 7, wherein the probe carrier is rotatable about at least one axis.

9. The apparatus of claim 8, and comprising data transmission lines in the probe carrier, which connect the image pick-up unit with a recorder connected to an image analyzing unit.

10. The apparatus of claim 8, and comprising at least one data transmitter connected to the probe carrier.

11. The apparatus of claim 8, and comprising at least one illuminator arranged on the probe carrier.

12. The apparatus of claim 1, wherein the surface of the component has restricted accessibility.

13. The apparatus of claim 12, wherein the component is a blade of a turbomachine.

14. The apparatus of claim 12, wherein the component is a blade arranged on a blisk of a gas turbine.

15. A method for inspection of a surface of a component, comprising:
- providing a traversing device;
- providing a probing device coupled to the traversing device and including two probe carriers provided in parallel arrangement, with a distance between the probe carriers exceeding a thickness of the component, and each probe carrier being smaller than a distance between the component and an adjacent component;
- providing at least one image pick-up unit fitted to each probe carrier;
- receiving image data from the surface of the component into the image pick-up units;
- feeding the image data from the image pick-up units to a recorder;
- storing the image data in the recorder; and
- forwarding the image data to an image analyzing unit.

16. The method of claim 15, and further comprising feeding the image data from the image pick-up units to the recorder by wireless transmission.

17. The method of claim 15, wherein the image analyzing unit automatically finds defects in the surface of the component.

18. The method of claim 17, wherein the image analyzing unit at least one of stores and indicates positions of surface defects in the form of three-dimensional coordinates.

19. The method of claim 18, wherein the image data is received continuously.

* * * * *